United States Patent [19]

Cerqueira

[11] Patent Number: 4,559,837
[45] Date of Patent: Dec. 24, 1985

[54] FAECES COLLECTION AND CONCENTRATION RECEIVER

[76] Inventor: Francisco L. Cerqueira, Rua Itacolomi, 180 ap 112, Sao Paulo, Brazil

[21] Appl. No.: 548,193

[22] PCT Filed: Sep. 23, 1982

[86] PCT No.: PCT/BR82/00013
§ 371 Date: Nov. 2, 1983
§ 102(e) Date: Nov. 2, 1983

[87] PCT Pub. No.: WO83/01194
PCT Pub. Date: Apr. 14, 1983

[51] Int. Cl.$^4$ ............................................. G01N 1/08
[52] U.S. Cl. ........................... 73/863.23; 73/864.44; 73/864.91; 422/101; 422/102
[58] Field of Search ........... 73/863.23, 864.44, 864.51, 73/864.91; 422/101, 102, 104; 128/760, 766, 767

[56] References Cited

U.S. PATENT DOCUMENTS

| 2,835,246 | 5/1958 | Boettger | 73/864.91 |
| 3,203,576 | 8/1965 | Wout et al. | |
| 3,518,164 | 6/1970 | Andelin et al. | |
| 3,811,326 | 5/1974 | Sokol | 356/246 |
| 4,221,225 | 9/1980 | Sloan | 73/863.23 |
| 4,300,404 | 11/1981 | Mehl et al. | |
| 4,357,240 | 11/1982 | Mehra et al. | |

FOREIGN PATENT DOCUMENTS

WO83/01194 4/1983 PCT Int'l Appl.

Primary Examiner—S. Clement Swisher
Attorney, Agent, or Firm—Michael J. Striker

[57] ABSTRACT

A faeces collection and concentration receiver, especially for parasitological examination, comprises a disposable receiver (1), a first cap immediately fastenable to the mouth of the receiver, a collecting-filtering device coupled between the receiver and the first cap, and a spout closed by a second cap.

11 Claims, 2 Drawing Figures

U.S. Patent       Dec. 24, 1985       4,559,837
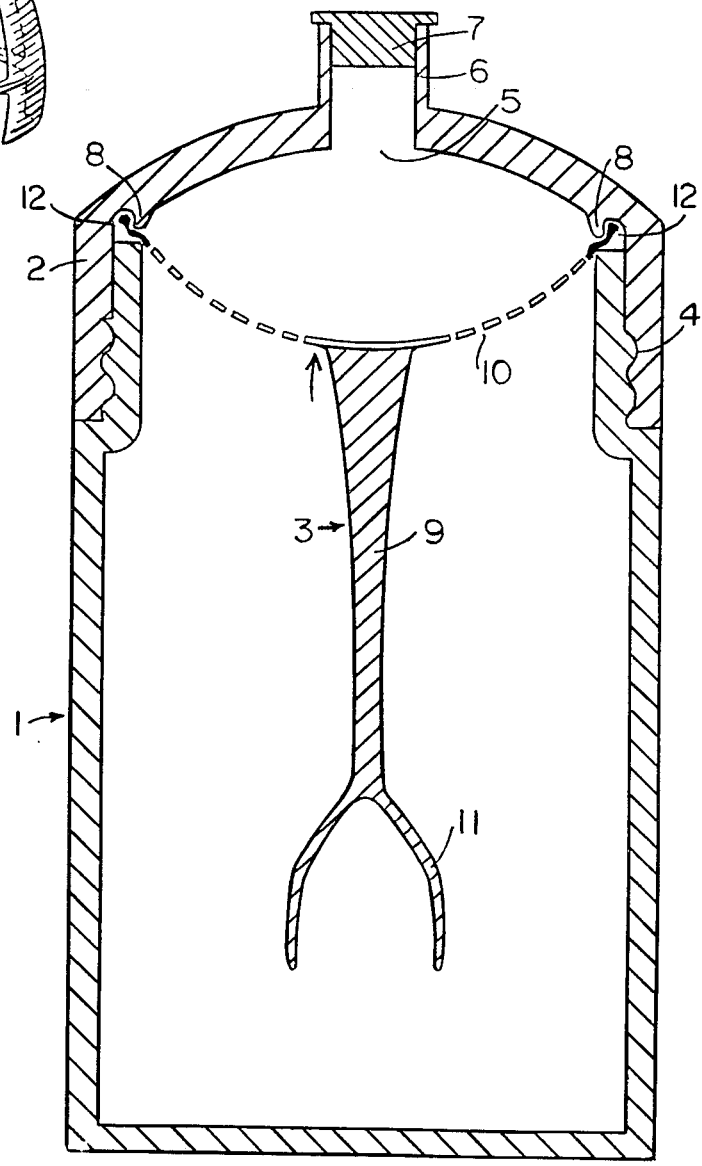
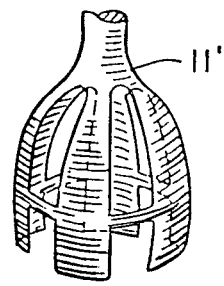
FIG. 2
FIG. 1

FAECES COLLECTION AND CONCENTRATION RECEIVER

BACKGROUND OF THE INVENTION

This present invention relates to a disposable receiver for the collection, preservation, transportation and preparation of faeces for the parasitological examination.

The preparation of faeces for the parasitological examination, named concentration technics, differs largely from one laboratory to the other, according to the laboratory's conditions and conveniences. The most used concentration technics involve the following phases:

1. Collection of a sample of faeces which is transferred to the receiver - usually a little can or plastic or glass container - which is then taken to the laboratory;
2. Transference of a portion of faeces into a flask or cup containing water;
3. Dilution of the faeces in the water, through agitation;
4. Filtration of the diluted faeces through a gauze or a plastic or wire net; and
5. Spontaneous sedimentation of the filtered product in a cone-shaped cup, or by centrifugation in a test tube.

During each of the above phases, the material is handled openly, using several devices, mainly improvised or adapted ones. The various methods proposed for enrichment of the samples to be examined (Faust, Willis, Baermann, Kato, MIFC, Ritchie, Rugai, AMS III, and direct examination), did not bother in simplifying such handling of the samples, which causes the operation to be troublesome, fastidious and anti-hygienical.

SUMMARY OF THE INVENTION

It is one of the objects of the present invention, to provide a receiver operative to eliminate several inconveniences which appear during the faeces collection and concentration phases. This result is achieved through the inclusion, in only one receiver, of all the necessary devices for the collection and concentration, which will then take place in a closed receiver.

Another object of this invention is to provide a receiver which is also disposable, formed by a minimum number of components, which can be manufactured easily and at low costs.

The novel features which are considered as characteristic for the invention are set forth in particular in the appended claims. The invention itself, however, both as to its construction and its method of operation, together with additonal objects and advantages thereof, will be best understood from the following description of specific embodiments when read in connection with the accopanying drawing.

BRIEF DESCRIPTION OF THE DRAWING

FIG. 1 is a longitudinal section view of the receiver; and

FIG. 2 is a partial perspective view of the faeces collector stick.

DETAILED DESCRIPTION OF THE PREFERRED EMBODIMENT

The device for collection and concentration of faeces comprises a semi-flexible plastic receiver, indicated by a number 1 on the attached drawing; a cap with special characteristics is denoted by numberal 2, which is fastenable to the mouth of the receiver through a thread 4, and a collecting-filtering device 3.

The cap 2 is internally concavous and is perforated at its centre 5, where a spout 6 is projected externally, forming a funnel; the spout 6 is closed by a cap 7; in the whole perimeter of cap 2 there is an internal ring-shaped salience 8, where the collecting-filtering device 3 is fastened by pressure.

The collecting-filtering device is a stick 9, which widens at one of its edges to form the sieve 10, and on the other edge to form the collector 11.

The border 12 of the sieve 10 is fastened to the cap 2, by pressure, on the already mentioned internal salience 8. The sieve 10 has orifices, with adequate dimensions, and is reinforced to avoid excessive flexibility. The other edge of the stick widens to form a device to collect the adequate amount of faeces, as indicated at 11' in FIG. 2.

HANDLING INSTRUCTIONS

1. Pour into the receiver an adequate volume of water or diluting solution;
2. Collect the faeces at the 11' edge of the collecting stick, holding it by the cap and pressing in its longitudinal direction the faecal matter;
3. Then introduce the collecting stick with the faeces into the receiver, and close;
4. Agitate the receiver until complete dilution of the faeces is achieved;
5. Open the spout 6 of the middle of the cap 2;
6. Turn the receiver upside down, introduce spout 6 in a test tube or a centrifuge tube, or even another cup. The diluted and filtered faeces will then fall into the tube or cup. Such process can be speeded up by pressing the sides of the receiver;
7. Separate then the receiver from the tube, close the spout 6 of the cap 2 and throw away;
8. Follow the conventional methods to prepare the material for examination.

ADVANTAGES

1. The faeces remain in a closed receiver until the filtering phase. This way, the bad odour spread throughout the room by handling the faeces is avoided;
2. Some phases in the faeces preparation are eliminated;
3. Reduces and simplifies labor;
4. There is no need for accessories such as sticks, gauze, pipets, cups, etc;
5. Largelly reduces the space necessary for the faeces examination in the laboratory;
6. Reduces the error margin in the identification of samples, by suppressing the transference of the faeces from one container to the other;
7. Reduces the possibility of cross-contamination;
8. The amount of faeces to be taken to be examined is standardized;
9. Being a disposable device it reduces the personnel for, and cuts expenses with, cleaning, washing and drying of containers and other accessories;
10. Reduces the personnel's contamination in the section;
11. Permits the use of preservation liquids, for examination of faeces long after collection.

Various modifications can be effected in the forms of the invention here described, taking into consideration that the essential in the idea of this invention, which the described and illustrated device presents, is the sieve fastened to the internal part of the cap of the receiver, for examination with the facilities and advantages described above. The author of the device reserves the right to modify such device according to practical conveniences and technical resources, being foreseen, among others, the following variations:

1. A built-in sieve in the cap of the receiver, forming a one-part piece;
2. A sieve fastened to the bottom or to the side wall of the receiver cap;
3. Adaptation of the sieve to the receiver cap through pressure or thread;
4. Adaptation of the cap to the receiver through pressure or thread;
5. Collecting stick separated from the sieve;
6. A spout manufactured separately for adaptation when using the device;
7. The spout fastened through pressure or thread;
8. Varied dimensions of the net and holes of the sieve;
9. A sieve manufactured with more than one layer, with equal or different small holes from one layer to the other;
10. Form of the sieve;
11. Form and dimensions of the collector;
12. Form and dimensions of the receiver;
13. Form and dimensions of the cap.

It will be understood that each of the elements described above, or two or more together, may also find a useful application in other types of faeces collection and concentration receivers differing from the types described above.

While the invention has been illustrated and described as embodied in a faeces collection and concentration receiver, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. Faeces collection and concentration receiver for parasitological examination, comprising, in combination, a disposable semi-flexible receiver, a first cap (2) fastenable immediately to a mouth of the receiver (1), and one collecting-filtering device (3) coupled between the receiver (1) and the first cap (2), said first cap having a spout (6) closed by a second cap (7).

2. Faeces collection and concentration receiver, according to claim 1, characterized by the first cap (2) which is fastenable to the receiver (1) through a thread (4) and which cap is internally concavous, and is perforated at its centre (5), where said spout is formed and projected externally from the receiver, forming a funnel, closed by the second cap.

3. Faeces collection and concentration receiver, according to claim 1, characterized by the collecting-filtering device (3) operative for the collection of faeces and its filtering after being diluted, which comprises a stick (9) which extends into said receiver and widens at one of its edges to form a sieve (10) of adequate netting, and at the other edge widens to form a device (11) operative for the collection of a proper amount of faeces or other material, the perimetral border of the sieve (12) being fastened to a ring-shaped salience (8) extended internally in the first cap.

4. Faeces collection and concentration receiver, according to claim 3, characterized by the collecting device (11) being of a semi-oval shape (11') with a central opening and side indentures.

5. Faeces collection and concentration receiver, according to claim 3, characterized by the sieve which is fastened to a bottom of the first cap.

6. Faeces collection and concentration receiver, according to claim 3, characterized by the sieve (10) being fastened to a side wall of the first cap.

7. Faeces collection and concentration receiver, according to claim 3, characterized by the sieve (10) which is built-in the the first cap.

8. Faeces collection and concentration receiver, according to claim 2, characterized by the first cap (2) which is fastenable to the receiver (1) by pressure.

9. Faeces collection and concentration receiver, according to claim 3, characterized by the collecting stick (9) which is separated from the sieve (10).

10. Faeces collection and concentration receiver according to claim 1, wherein said spout is formed of one piece with the first cap.

11. Faeces collection and concentration receiver according to claim 1, wherein said collecting-filtering device is accommodated in said receiver.

* * * * *